(12) United States Patent
Park

(10) Patent No.: US 10,143,549 B2
(45) Date of Patent: Dec. 4, 2018

(54) COMPOSITE VALVED GRAFT COMPRISING DOUBLE SEWING CUFFS

(71) Applicants: Gil Medical Center, Incheon (KR); Gachon University of Industry-Academic Cooperation Foundation, Seongnam-si, Gyeonggi-do (KR)

(72) Inventor: Chul Hyun Park, Yongin-si (KR)

(73) Assignees: GIL MEDICAL CENTER, Incheon (KR); GACHON UNIVERSITY OF INDUSTRY-ACADEMIC COOPERATION FOUNDATION, Seongnam-si, Gyeonggi-do (KR)

( * ) Notice: Subject to any disclaimer, the term of this patent is extended or adjusted under 35 U.S.C. 154(b) by 0 days.

(21) Appl. No.: 14/411,837

(22) PCT Filed: Oct. 10, 2014

(86) PCT No.: PCT/KR2014/009512
§ 371 (c)(1),
(2) Date: Dec. 29, 2014

(87) PCT Pub. No.: WO2016/021767
PCT Pub. Date: Feb. 11, 2016

(65) Prior Publication Data
US 2017/0135812 A1    May 18, 2017

(30) Foreign Application Priority Data
Aug. 5, 2014 (KR) .................. 10-2014-0100529

(51) Int. Cl.
*A61F 2/24*        (2006.01)
*A61B 17/04*       (2006.01)
(Continued)

(52) U.S. Cl.
CPC ........ *A61F 2/2409* (2013.01); *A61B 17/0057* (2013.01); *A61B 17/04* (2013.01);
(Continued)

(58) Field of Classification Search
USPC .................................................. 623/1.1–2.4
See application file for complete search history.

(56) References Cited

U.S. PATENT DOCUMENTS 5,258,023 A * 11/1993 Reger .................. A61F 2/2409
                                                        623/2.18
5,469,868 A    11/1995 Reger
(Continued)

FOREIGN PATENT DOCUMENTS

JP     2012-205909    10/2012
WO     2012/162522 A2 11/2012

OTHER PUBLICATIONS

International Search Report dated Apr. 20, 2015 in corresponding PCT/KR2014/009512 filed on Oct. 10, 2014.

*Primary Examiner* — Yashita Sharma
(74) *Attorney, Agent, or Firm* — Hovey Williams LLP

(57) ABSTRACT

Disclosed is an artificial valved conduit that is a composite valved graft comprising double sewing cuffs, which can be easily used in aortic root replacement. The composite valved graft comprises a valve and a conduit part connected to the valve. The conduit part comprises a sewing cuff positioned on the outer circumference thereof. The sewing cuff comprises a first sewing cuff and a second sewing cuff positioned below the first sewing cuff. Accordingly, a double suture is easily performed, so that it is possible to prevent the loss of blood after a surgery and to reduce surgical time at the same time.

8 Claims, 6 Drawing Sheets

(51) Int. Cl.
 *A61F 2/06* (2013.01)
 *A61B 17/00* (2006.01)
(52) U.S. Cl.
 CPC ........... *A61F 2/06* (2013.01); *A61F 2/064* (2013.01); *A61F 2/2403* (2013.01); *A61F 2/2418* (2013.01); *A61F 2210/0076* (2013.01); *A61F 2220/0008* (2013.01)

(56) References Cited

U.S. PATENT DOCUMENTS

| | | |
|---|---|---|
| 5,908,451 A | 6/1999 | Yeo |
| 6,951,573 B1 | 10/2005 | Dilling |
| 2006/0195184 A1 | 8/2006 | Lane et al. |
| 2007/0016285 A1 | 1/2007 | Lane et al. |
| 2008/0082161 A1 | 4/2008 | Woo |
| 2014/0081391 A1 | 3/2014 | Ruyra-Baliarda et al. |
| 2016/0067042 A1* | 3/2016 | Murad ............... A61F 2/2409 623/2.17 |

* cited by examiner

COMPOSITE VALVED GRAFT COMPRISING DOUBLE SEWING CUFFS

RELATED APPLICATIONS

This application claims priority to PCT International Patent Application No. PCT/KR2014/009512, filed Oct. 10, 2014, which claims the priority benefit to Korean Patent Application No. 10-2014-0100529, filed on Aug. 5, 2014, both of which are hereby incorporated by reference in their entirety.

BACKGROUND OF THE INVENTION

1. Field of the Invention

The present invention relates to a composite valved graft, and more particularly, to an artificial valved conduit that is a composite valved graft comprising double sewing cuffs, which can be easily used in aortic root replacement.

2. Description of the Conventional Art

In general, aortic root replacement is a surgery in which, when aortic valve regurgitation is accompanied in a patient suffering from ascending aortic aneurysm that intrudes the patient's aortic root, the lesion part is excised, and an artificial valved conduit that is a composite valved graft is used.

Each of the existing composite valved grafts used in the aortic root replacement is generally configured with a sewing cuff, an artificial valve, and a conduit part connected thereto. In replacement using such a composite valved graft, when an anastomosis is performed, a medical specialist closely sutures a sewing cuff of the composite valved graft and a cut part of a blood vessel relying upon manual work. However, problems frequently arise in the anastomosis stage.

The aortic root replacement, because of its characteristics, involves operating on a wide area. In the aortic root replacement, after the aortic root is excised, an artificial valve and artificial blood vessels are anastomosed at a deep part of the heart, and entrance parts of the left and right coronary arteries are anastomosed. As such, the number of parts involved in anastomosis is greater than that in heart surgery, and hence lengthening the operating time of the aortic root replacement.

Aortic root replacement is not only complicated but, also a type of surgery in which it is difficult to detect the loss of blood after anastomosis. In relation to the aortic root replacement, several methods for reducing the loss of blood have been studied and proposed, but the frequency of bleeding is reported as 5 to 13% (Long-Term Mortality and Morbidity after Button Bentall Operation, J Card Surg, 2013, Vol.28; pp.280-284).

If blood loss occurs where anastomosis has been performed, several problems occur. In this case, such problems include a need for a reoperation, extension of extracorporeal circulation time, and heart ischemia time, transfusion of a large amount of blood, and the like. This has a negative impact on the patient financially as well as on the patient's health. Particularly, when bleeding occurs at is the rear of a proximal conduit, it may be difficult to perform re-anastomosis.

As a method for preventing the loss of blood, a method has been conceived of surrounding a transplanted conduit with the patient's aortic wall, a method of connecting the aortic wall, and the right atrium, a method of anastomosing the aortic wall to the artery conduit, performing reinforcement anastomosis surgery using self-pericardium, and the like. However, a large number of disadvantages have been reported regarding these methods.

Conventionally, sewing cuffs were devised to overcome disadvantages in the anastomosis surgery and to minimize side effects. As an example, U.S. Pat. No. 6,351,573 discloses various types of sewing cuffs surrounding the outer circumference of a valve. However, the disclosed sewing cuff is made of a semi-rigid material so that suturing is performed only when a suture fiber passes through holes provided in the sewing cuff. Therefore, there is an inconvenience in that the suture fiber is to pass through each hole for the purpose of airtight suturing. The disclosed sewing cuff additionally provides an adherence band which can be connected to the circumference of a valve, so that it is possible to more easily prevent the loss of blood. However, the sewing cuff varies widely in applicability according to surgical parts and situations. Since the shape of the sewing cuff is complicated, the sewing cuff can be easily used after a user is good at the use of the sewing cuff, and the efficiency of the sewing cuff may deteriorate with time. In addition, there is an inconvenience in that effects of a technique disclosed according to each surgical situation can be obtained only when the user is fully aware of usage according to the kind of sewing cuff, and it is very difficult to apply the sewing cuff to actual clinical practice.

As another example, in PCT Patent Publication No. WO 2012-162522, the sewing cuff comprises one or more sewing cuffs on the outer circumference of an artificial valve in order to perform a more efficient and convenient anastomosis surgery between the valve and an annulus. A first sewing cuff is positioned on the outer circumference of the valve and has a height that is not less than 50% of the height of the valve in a closed state. A second sewing cuff narrower than the first sewing cuff is positioned on the outer circumference of the first sewing cuff. The second sewing cuff having a crown shape or a shape with upper and lower parts alternately placed in the vertical direction is positioned on the first sewing cuff. Thus, it is possible to prevent the deformation of a blood vessel surface that is caused when human tissue is aligned with the sewing cuff during the anastomosis surgery. Accordingly, the sewing cuff can be more easily used in suturing. That is, since the aortic annulus in a human body is not formed in a horizontal shape but anatomically formed in a fan type crown shape, the sewing cuff of the artificial valve, disclosed in PCT Patent Publication No. WO 2012-162522, is manufactured in the same shape suitable for the aortic annulus, so that it can be expected that the difficulty in nadir suture of the annulus will be dissolved.

However, the substantially efficient application range of the sewing cuff is limited to the annular nadir of tissue valve root by the special shape and position of the second sewing cuff. As a result, due to the special shape of the second sewing cuff, there is still an inconvenience in that the human tissue imust be aligned with the sewing cuff. Meanwhile, aortic valve regurgitation is generally accompanied in artificial blood vessel replacement comprising a valve. In this case, although the crown-shaped sewing cuff has a shape different from those of the existing sewing cuffs, when it is substantially applied, a big difference in view of efficiency for suppressing the aortic valve regurgitation cannot be expected just as it is with the traditional sewing cuffs because double suturing is not performed. Furthermore, since the annulus is expanded during an actual surgery, the necessity of having to use a crown-shaped sewing cuffless-ens.

As described above, there have been proposed sewing cuffs on the outer circumferences of various types of artificial valves in order to prevent the loss of blood after an anastomosis surgery is performed. However, applicable situations are limited due to the complicated or special shape of the sewing cuff, and there is an inconvenience in that a user must familiarize oneself with the usage of the sewing cuff beforehand. Although the loss of blood can be reduced by using the sewing cuff, because it may take a longer time to use the sewing cuff the efficiency is lessened by comparison. The conventional composite valved grafts and the sewing cuffs included therein, have limits when it comes to solving these problems.

PRIOR ART DOCUMENTS

Patent Documents (Patent Document 1) U.S. Pat. No. 6,951,573 B1
(Patent Document 2) WO 2012-162522 A2

Non-Patent Documents (Non-Patent Document 1) Bentall H, De Bono A. A technique for complete replacement of the ascending aorta. Thorax 1968;23:338-339

(Non-Patent Document 2) Cabrol C, Pavic A, Gandjbakheh I, Villemot J. P., Guiraudon G, Laughlin L, Etievent P, Cham B. Complete replacement of ascending aorta with reimplantation of coronary arteries. Thorac Cardiovasc Surg 1981; 81:309-315

(Non-Patent Document 3) Copeland J. G. III, Rosada L. J., Snyder S. L. New technique for improving hemostasis in aortic root replacement with composite graft. Ann Thorac Surg 1993;55:1027-1029

(Non-Patent Document 4) Mohite P. N., Thingnam S. K., Puri S, Kulkarni P. P. Use of pericardial strip for reinforcement of proximal anastomosis in Bentall's procedure Interact Cardiovasc Thorac Surg 2010;11:527-528

SUMMARY OF THE INVENTION

Therefore, an aspect of the detailed description is to provide a composite valved graft which prevents the loss of blood after an anastomosis surgery is performed, and is convenient and simple to use.

Another aspect of the detailed description is to provide a composite valved graft which can be applied to various cases in aortic root replacement using the composite valved graft or blood vessel replacement including a valve.

Still another aspect of the detailed description is to provide a composite valved graft configured to reduce surgical time in the existing surgeries in which a double suture is performed.

To achieve these and other advantages and in accordance with the purpose of this specification, as embodied and broadly described herein, a composite valved graft comprises: a valve; and a conduit part connected to the valve, wherein the conduit part comprises a sewing cuff positioned on the outer circumference thereof, and the sewing cuff comprises a first sewing cuff and a second sewing cuff positioned below the first sewing cuff. The first and second sewing cuffs are spaced apart from the first opening of the conduit part.

The valve may comprise a valve part having a valve leaflet and a valve leaflet support, and a hollow opening positioned around the outside of the valve part to accommodate the valve part therein. The valve leaflet support may be connected to the inner surface of the opening to support the valve leaflet.

Each of the first and second sewing cuffs may have a continuous ring shape.

The first and second sewing cuffs may be positioned in parallel while being spaced apart from each other.

The first and second sewing cuffs may be extended from the same position on the outer circumference of the conduit part.

As described above, according to the present invention, the composite valved graft comprises the double sewing cuffs that facilitate double suture, so that it is possible to efficiently prevent the loss of blood after surgery.

Further, the usage of components and double cuffs of the composite valved graft is simple, so that it does not take a long time to become fully familiar with usage.

Further, since the double cuffs according to the present invention can be applied in various cases wherein composite valved grafts are used in aortic root replacement or a valve is included in a blood vessel replacement, the scope of applicability is wide.

Further, the composite valved graft comprises the double cuffs, so that the time of the existing anastomosis surgery is reduced, thereby obtaining a positive surgical result.

Further scope of applicability of the present application will become more apparent from the detailed description given hereinafter. However, it should be is understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWING

The accompanying drawings, which are included to provide a further understanding of the invention and are incorporated in and constitute a part of this specification, illustrate exemplary embodiments and together with the description serve to explain the principles of the invention.

In the drawings.

DETAILED DESCRIPTION OF EXEMPLARY EMBODIMENTS

Figure 1:
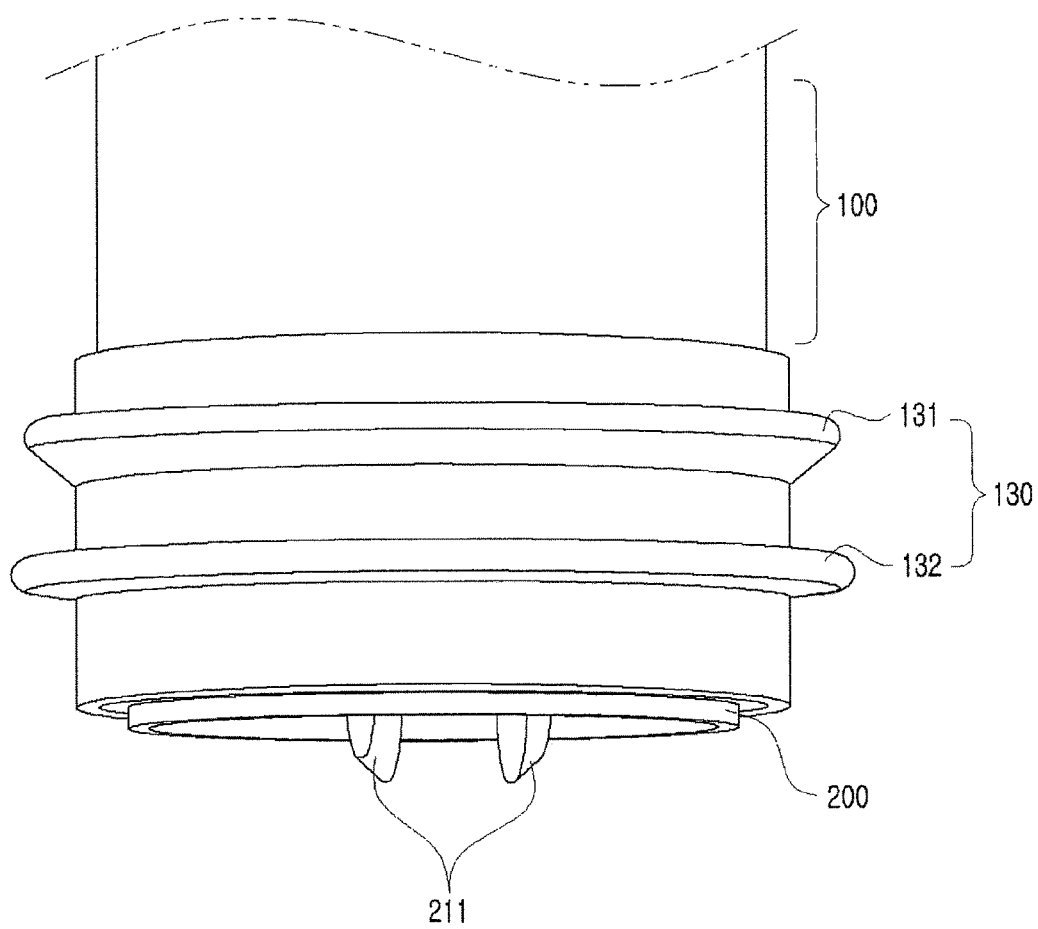
FIG. 1 is a perspective view illustrating a composite valved graft according to a first embodiment of the present invention.

Hereinafter reference will now be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents, and other embodiments, which may be included within the spirit and scope of the invention as defined by the appended claims.

In the present invention, a composite valved graft comprising double sewing cuffs will be described as an example. However, the same principle can be applied to other apparatuses other than the composite valved graft. Therefore, it will be obvious that the scope of the present invention defined by the appended claims can be applied to the other apparatuses having the double sewing cuffs, to which the same principle is applied.

Components constituting the present invention, when necessary, may be used in a single body or may be used separately from one another. Further, some components may be omitted.

Exemplary embodiments of the composite valved graft comprising the double sewing cuffs according to the present invention will be described with reference to FIGS. 1 to 6. In the drawings, the thicknesses of lines, the sizes of is components, or the like may be exaggerated for clarity and convenience of explanation. The following terms are terms which are defined based on functionality in the present invention. Since the meanings of these terms may vary depending on a user or operator's intention or custom, the definitions of these terms should be determined based on the entire content of the present specification that describes the present invention.

1. Description of Configuration of Composite Valved Graft

Hereinafter, an embodiment of the composite valved graft according to the present invention will be described with reference to the accompanying drawings.

First, the entire configuration of the composite valved graft will be described with reference to FIG. 1.

The composite valved graft according to the embodiment of the present invention comprises a valve 200 and a conduit part 100 connected to the valve 200. The conduit part 100 comprises a sewing cuff 130 positioned to be connected to the outer circumference thereof. The sewing cuff 130 comprises a first sewing cuff 131 and a second sewing cuff 132 positioned below the first sewing cuff 131.

Figure 2:
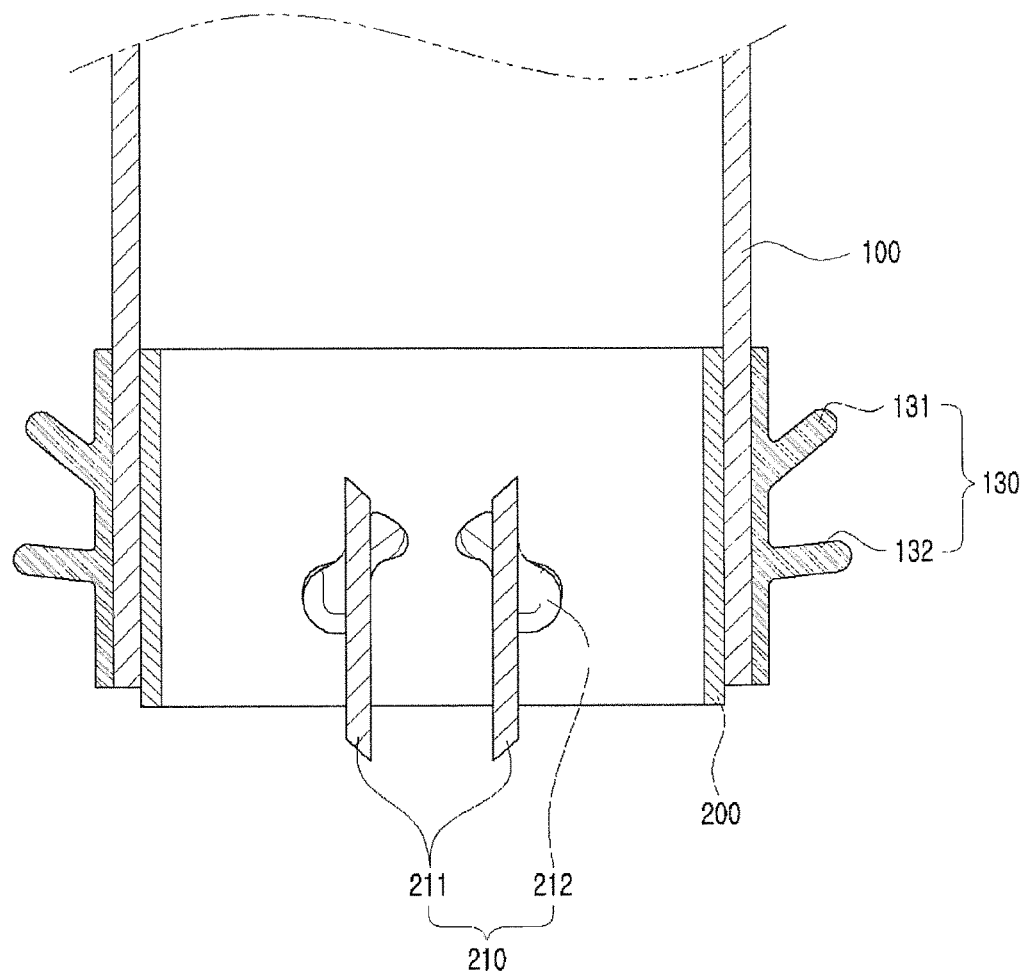
FIG. 2 is a longitudinal sectional view of FIG. 1.

The conduit part 100 and the valve 200 will be described in more detail with reference to FIGS. 2 and 3.

In the conventional composite valved graft, when a user attempted a double suture for preventing the loss of blood, the aortic wall was directly sutured to the conduit part 100 by way of a second suture, making it difficult to perform the suture, thereby lengthening surgical time, and resulting in excessive bleeding.

According to the embodiment of the present invention that is effective in reducing surgical time by overcoming these problems, each of the first and second sewing cuffs 131 and 132 of the conduit part 100 has a ring shape surrounding the outer circumference of the conduit part 100. The sewing cuff is manufactured from fiber, elastic material, semi-rigid material, or similar, formed of materials with properties advantageous for easy suturing. The first sewing cuff 131 is positioned above the second sewing cuff 132, protruding in a continuous form In this state, the first and second sewing cuffs 131 and 132 may be positioned to be parallel to each other while being spaced apart (FIG. 2).

Figure 3:
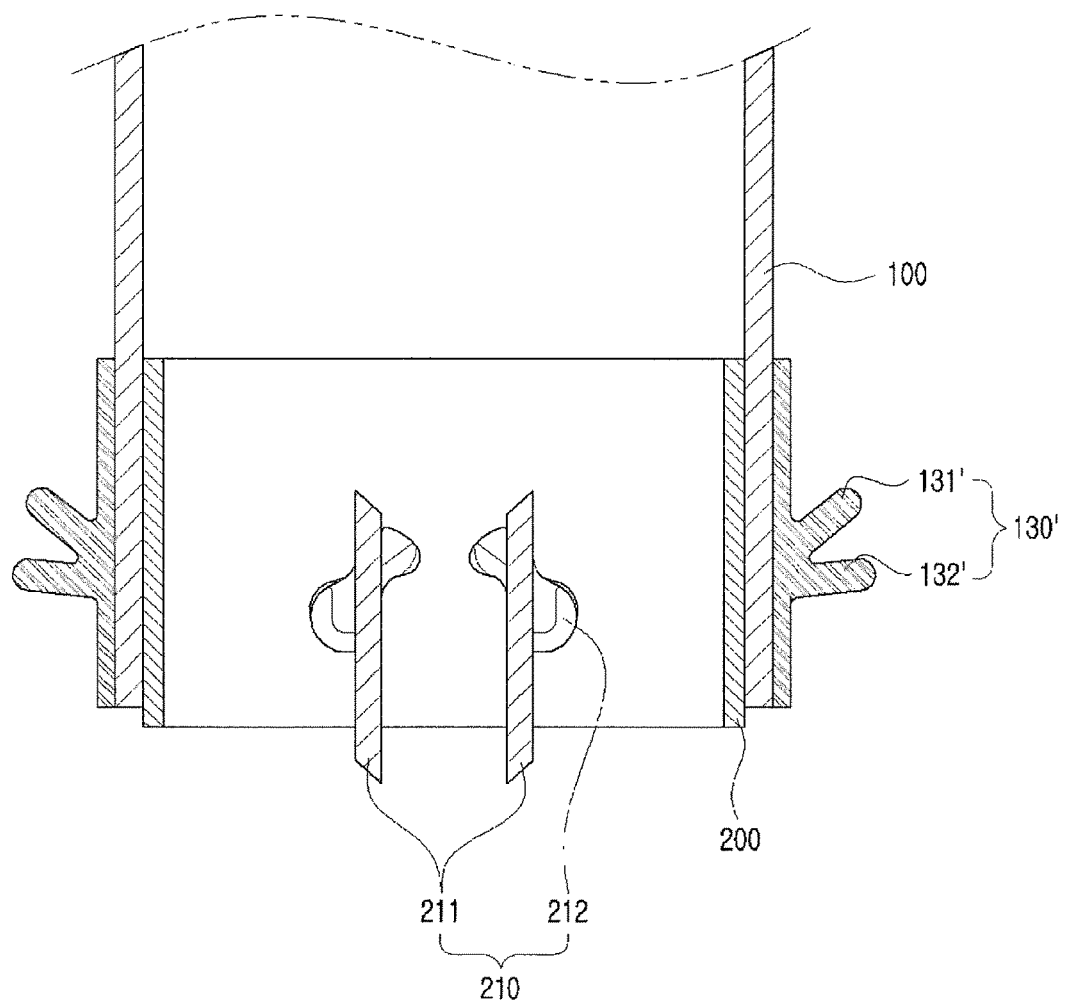
FIG. 3 is a longitudinal sectional view illustrating a composite valved graft according to a second embodiment of the present invention.

According to a modified embodiment, in a ring-shaped sewing cuff 130' surrounding the outer circumference of a conduit part 100', first and second sewing cuffs 131' and 132' may not be parallel to each other, and may be extended from the same position of the outer circumference of the conduit part 100' (FIG. 3). The more advantageous form among the two sewing cuffs 130 and 130' may be selected according to the form of human tissue on which replacement is to be performed and according to the surgical situation.

Figure 6:
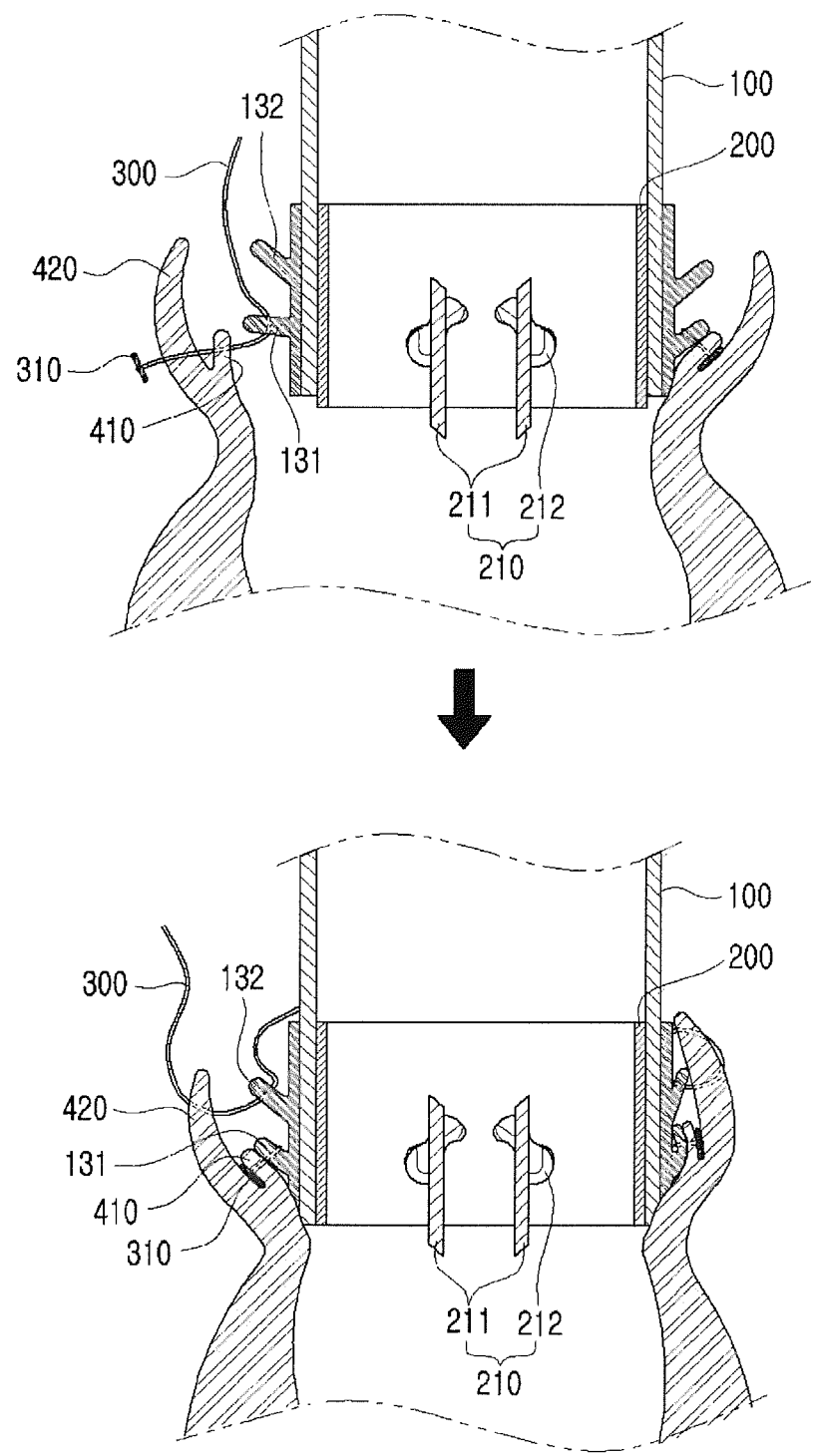
FIG. 6 is a longitudinal sectional view illustrating a process in which the composite valved graft is applied according to the first embodiment of the present is invention.

The double suture, to which the sewing cuff 130 or 130' according to the embodiment is applied, may comprise two overall steps. In the first step, the composite valved graft may be connected to a portion of an excised human tissue 400 (e.g., an aortic annulus 410) along the first sewing cuff 131 or 131'. In the second step, the composite valved graft may be connected to the other portion of the human tissue 400 (e.g., an aortic end 420) along the second sewing cuff 132 or 132' (FIG. 6).

In order to efficiently perform these steps, the thicknesses, extended lengths, positions, and the like, of the first sewing cuff 131 or 131' and the second sewing cuff 132 or 132' are not limited, but the second sewing cuff 132 or 132' is preferably formed so that the suture operation of the second sewing cuff 132 or 132' does not become inconvenient due to the first sewing cuff 131 or 131'.

The sewing cuff 130 or 130' preferably has a ring shape which is continuous and not curved. Accordingly, the disposition state of the sewing cuff 130 or 130' is hardly influenced by the shape of the end of a human tissue excised in a general aortic root replacement, and thus the sewing cuff 130 or 130' can be flexibly applied. Unlike the present invention, if a sewing cuff has a discontinuous ring shape or a shape including a special curve, the anastomosis surgery must be performed along the shape of the sewing cuff. Hence, as the position at which the sewing cuff is disposed becomes more important, the suturing process may take a longer time, and the surgical part to which the sewing cuff can be applied is limited.

The valve leaflet 211 and the valve leaflet support 212 are accommodated in the hollow opening 220. The valve leaflet support 212 is connected to the inner surface of the opening 220 to support the valve leaflet 211. The valve leaflet 211 is composed of two members, and each of them rotates about the valve leaflet support 212 that supports them as an axis. Thus, the valve leaflet 211 repeats opening and closing according to the flow of blood in one direction. In this manner, the valve leaflet 211 prevents blood from being regurgitated in the valve 200.

2. Description of Application of Composite Valved Graft

Hereinafter, an application of the composite valved graft according to the embodiment of the present invention will be described with reference to FIGS. 4 to 6.

First, the composite valved graft is prepared, and identify whether the conduit part 100 and the valve 200 are well connected to each other. is Subsequently, suture thread 300 and pledget 310 for anastomosing the human tissue 400 and the composite valved graft are prepared. Here, the human tissue 400 indicates the human tissue as a concept of including the aortic annulus 410.

The composite valved graft is disposed so that the sewing cuff 130 or 130' can be easily connected to a portion of the excised human tissue 400 at an appropriate position where replacement has to be performed (e.g., the first sewing cuff 131 or 131' is connected to the patient's aortic annulus 410, and the second sewing cuff 132 or 132' is connected to the aortic end 420 which is the other portion of the excised human tissue 400).

In this state, a portion of the composite valved graft, at which the sewing cuff 130 or 130' is positioned, is preferably positioned to be inserted into the excised human tissue 400.

First, the suture thread 300 is passed through the first sewing cuff 131 or 131' to perform a thorough, continuous suture as the human tissue 400 (preferably, the aortic annulus 410) is gradually adhered closely to the first sewing cuff 131 or 131'. In this process, the pledget 310 is preferably used to connect more closely between the excised aortic annulus 410 of the human tissue and the composite valved graft.

Figure 4:
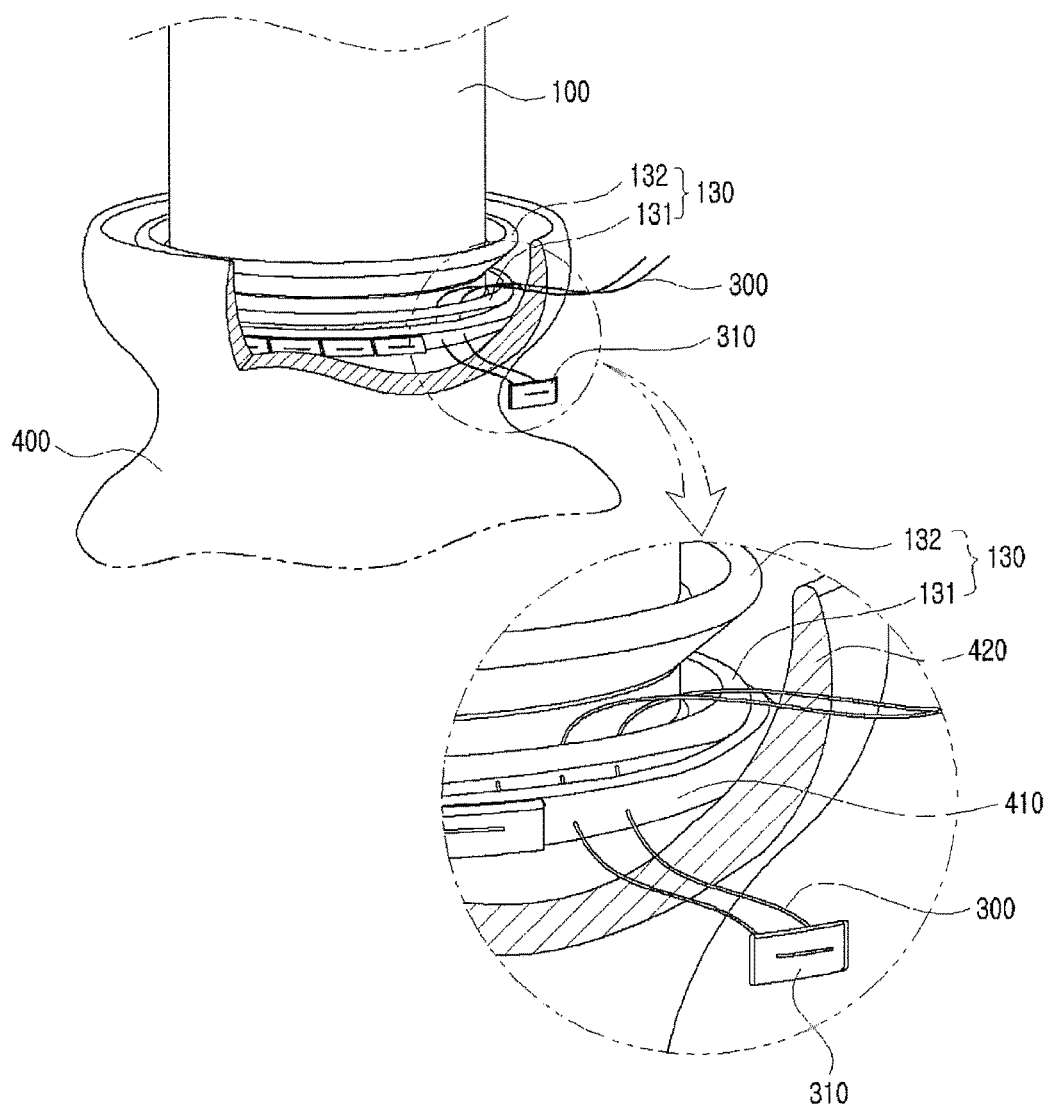
FIG. 4 shows perspective and enlarged perspective views illustrating that a first sewing cuff of the composite valved graft is applied according to the first embodiment of the present invention.

In a case where a double suture is performed using the pledget 310, the suture thread 300 sequentially passes through the pledget 310, the human tissue 400 and the sewing cuff 130 or 131' in order, and then passes through them in reverse order, thereby obtaining a closer connection (FIG. 4).

Figure 5:
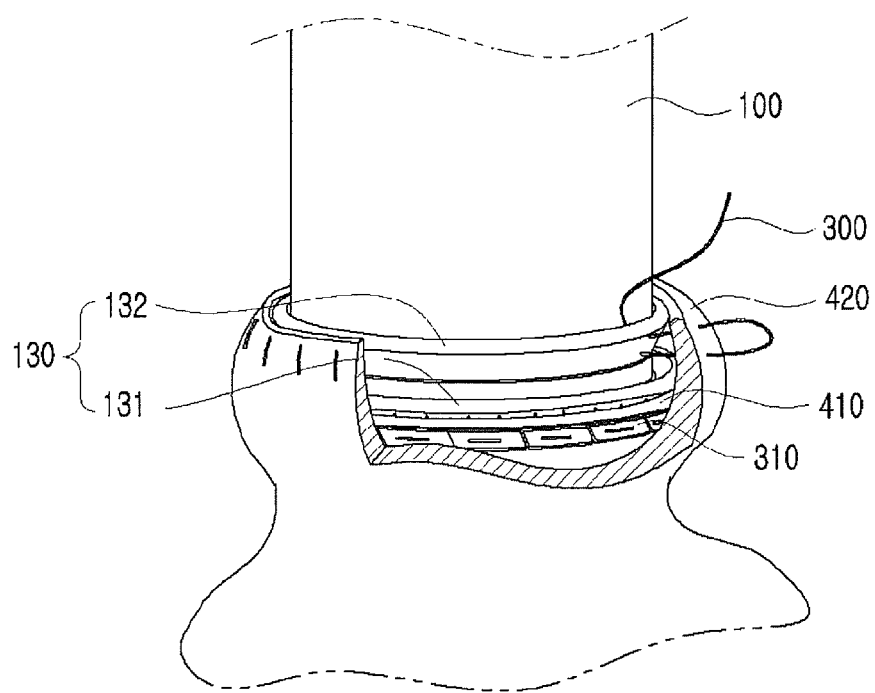
FIG. 5 shows perspective and enlarged perspective views illustrating that a second sewing cuff of the composite valved graft is applied according to the first embodiment of the present invention.

After the first sewing cuff 131 or 131' is connected to at least a portion of the excised human tissue 400 (e.g., at least a portion of the aortic annulus 410), a double suture is performed by passing the suture thread 300 through another is portion (e.g., the aortic end 420) of the human tissue 400 and the second sewing cuff 132 or 132' (FIG. 5). By making double suturing possible in this way, the anastomosis is efficiently performed, so that postoperative blood loss may be prevented.

In this state, it will be understood by a skilled technician in the corresponding field that the process should be flexibly performed according to the necessity of continuous suture, and the number of suture thread 300 or the sutured form of the suture thread 300 is not limited in the use of the suture thread 300.

The foregoing embodiments and advantages are merely exemplary and are not to be construed as limiting the present disclosure. The present features can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A composite valved graft for aortic root replacement in which a portion of the aorta is resected and replaced, said composite valved graft comprising;
a valve; and
a conduit part connected to the valve, wherein the conduit part presents a first opening and the valve is positioned within the first opening,
wherein the conduit part comprises a ring-shaped sewing cuff surrounding and connected to the outer circumference of the conduit part, wherein the sewing cuff comprises a first sewing cuff and a second sewing cuff positioned below the first sewing cuff, wherein the first and second sewing cuffs are spaced apart from the first opening of the conduit part,
wherein the distance between the first sewn cuff and the second sewing cuff is increased as they outwardly extend; and
wherein the first sewing cuff and the second sewing cuff are configured to be connected to different portions of human tissue.

2. The composite valved graft, of claim 1, wherein the valve comprises a valve part having a valve leaflet and a valve leaflet support, and a hollow opening positioned around the outside of the valve part to accommodate the valve part therein, and
wherein the valve leaflet support is connected to the inner surface of the opening to support the valve leaflet.

3. The composite valved graft of any one of claims 1 and 2, wherein each of the first and second sewing cuffs has a continuous ring shape.

4. The composite valved graft of claim 3, wherein the first and second sewing cuffs are positioned parallel to each other while being spaced apart.

5. The composite valved graft of claim 3, wherein the first and second sewing cute extend from the same position on the outer circumference of the conduit part.

6. A composite valved graft for full aortic root replacement in which a portion of the aorta is resected and replaced, wherein the composite valved graft comprises:
a valve; and
a conduit part connected to the valve, wherein the conduit part presents a first opening and the valve is positioned within the first opening
wherein the conduit part comprises a ring-shaped sewing cuff surrounding and connected to the outer circumference of the conduit part, wherein the sewing cuff comprises a first sewing cuff and a second sewing cuff positioned below the first sewing cuff, wherein the first and second sewing cuffs are spaced apart from the first opening of the conduit part,
wherein the distance between the first sewing cuff and the second sewing cuff is increased as they outwardly extend; and
wherein the first and second sewing cuffs extend from the same position on the outer circumference of the conduit part.

7. The composite valved graft of claim 6, wherein the first and second sewing cuffs are manufactured of any one of fiber, elastic material and semi-rigid material.

8. The composite valved graft of claim 6, wherein the first and second sewing cuffs are integrally manufactured with each other.

* * * * *